United States Patent [19]

Connor et al.

[11] 4,138,550

[45] Feb. 6, 1979

[54] **DIACYLOXYACIDS DERIVED FROM ACID S, AN ANTIBIOTIC PRODUCED BY *POLYANGIUM CELLULOSUM* VAR. *FULVUM***

[75] Inventors: David T. Connor, Parsippany; Samuel M. Ringel, Rockaway; Sidney Roemer, Flanders; Maximillian Von Strandtmann, Rockaway, all of N.J.

[73] Assignee: Warner-Lambert Company, Morris Plains, N.J.

[21] Appl. No.: 765,568

[22] Filed: Feb. 4, 1977

Related U.S. Application Data

[63] Continuation-in-part of Ser. No. 693,400, Jun. 7, 1976, abandoned.

[51] Int. Cl.² ............................................. C09B 23/00
[52] U.S. Cl. ................................... 542/430; 424/115; 424/121; 424/122

[58] Field of Search ..................... 260/240 R; 424/115, 424/121, 122; 542/430, 447

[56] References Cited

U.S. PATENT DOCUMENTS

| | | | |
|---|---|---|---|
| 3,651,216 | 3/1972 | Ringel et al. | 424/115 |
| 3,804,948 | 4/1974 | Strandtmann et al. | 424/122 |
| 4,001,398 | 1/1977 | Connor et al. | 424/122 |
| 4,009,261 | 2/1977 | Connor et al. | 424/122 |
| 4,016,257 | 4/1977 | Connor et al. | 424/122 |

*Primary Examiner*—Paul F. Shaver
*Attorney, Agent, or Firm*—Albert H. Graddis; Frank S. Chow; Anne M. Kelly

[57] ABSTRACT

The present invention relates to diacyloxyacids derived from the antibiotic substance, designated acid S, produced by *Polyangium cellulosum* var. *fulvum* (ATCC No. 25532), and to processes for their production. The diacyloxyacids derivatives of acid S of this invention are useful as antifungal and antibacterial agents.

5 Claims, 3 Drawing Figures

ACID S DIFORMATE

FIG. 2 ACID S DIPROPIONATE

ACID S DIBUTYRATE

DIACYLOXYACIDS DERIVED FROM ACID S, AN ANTIBIOTIC PRODUCED BY *POLYANGIUM CELLULOSUM* VAR. *FULVUM*

CROSS REFERENCE TO RELATED APPLICATIONS

This application is a continuation-in-part of U.S. application Ser. No. 693,400, filed June 7, 1976 now abandoned.

SUMMARY OF THE INVENTION

The present invention relates to diacyloxyacids derived by structurally modifying the substance known as acid S, a potent antibiotic isolated from *Polyangium cellulosum* var. *fulvum* (ATCC No. 25532). Specifically, the present invention relates to diacyloxyacids having the following formula is I:

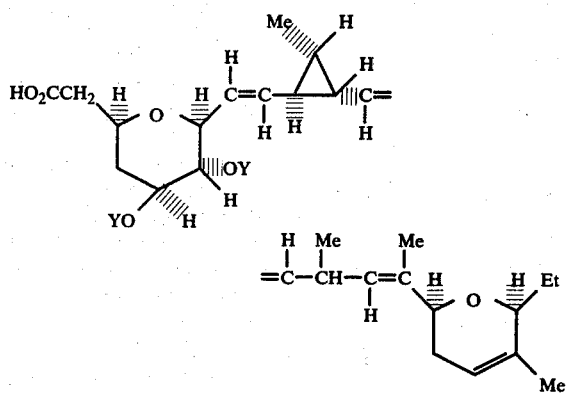

wherein Y in each instance is an acyl group derived from formic acid or a lower alkyl carboxylic acid having from 3 to 7 carbon atoms. Preferably Y is an acyl group derived from formic acid or a lower alkyl carboxylic acid having from 3 to 4 carbon atoms. The diacyloxyacids of acid S are prepared by reacting acid S with the appropriate acid anhydride in pyridine. To prepare acid S diformate, the acid S is reacted with triphenylphosphine and bromine in dimethylformamide.

BRIEF DESCRIPTION OF THE DRAWINGS

The infrared spectra of respresentative diacyloxy derivatives of acid S of this invention are illustrated in FIGS. 1, 2 and 3 of the drawings.

Figure 1:
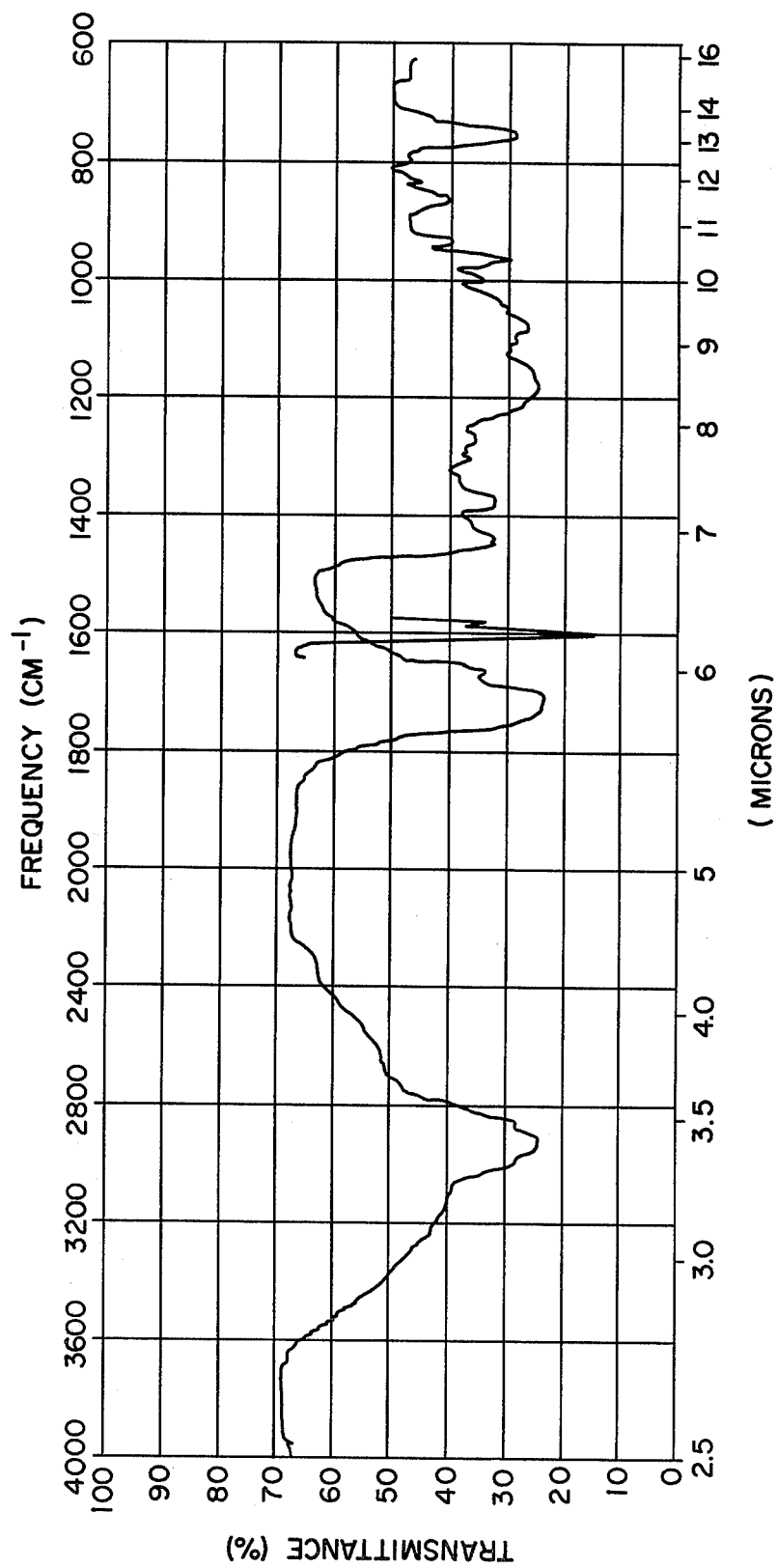
FIG. 1 depicts the infrared spectrum of acid S diformate.
Figure 2:
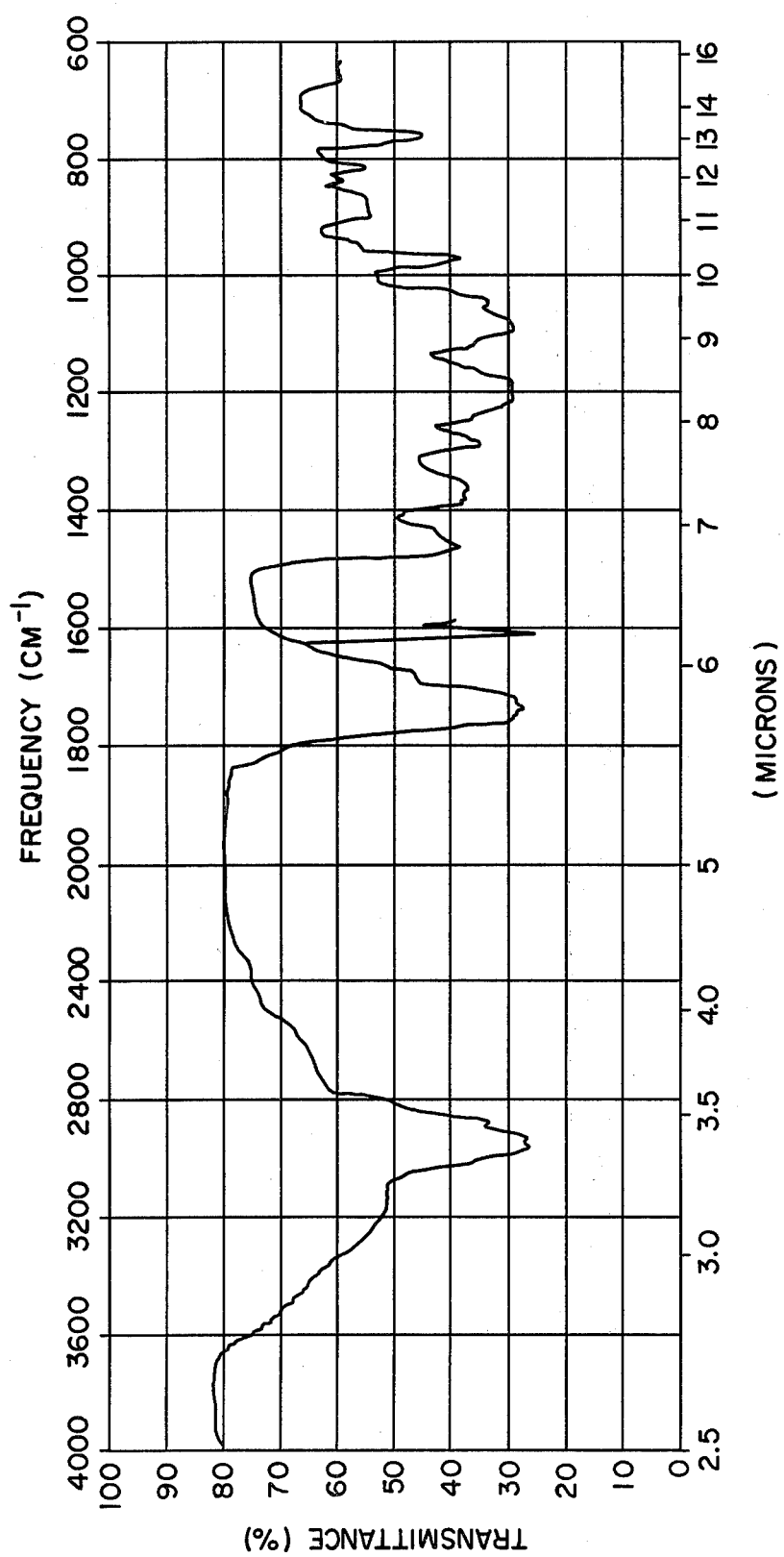
FIG. 2 depicts the infrared spectrum of acid S dipropionate.
Figure 3:
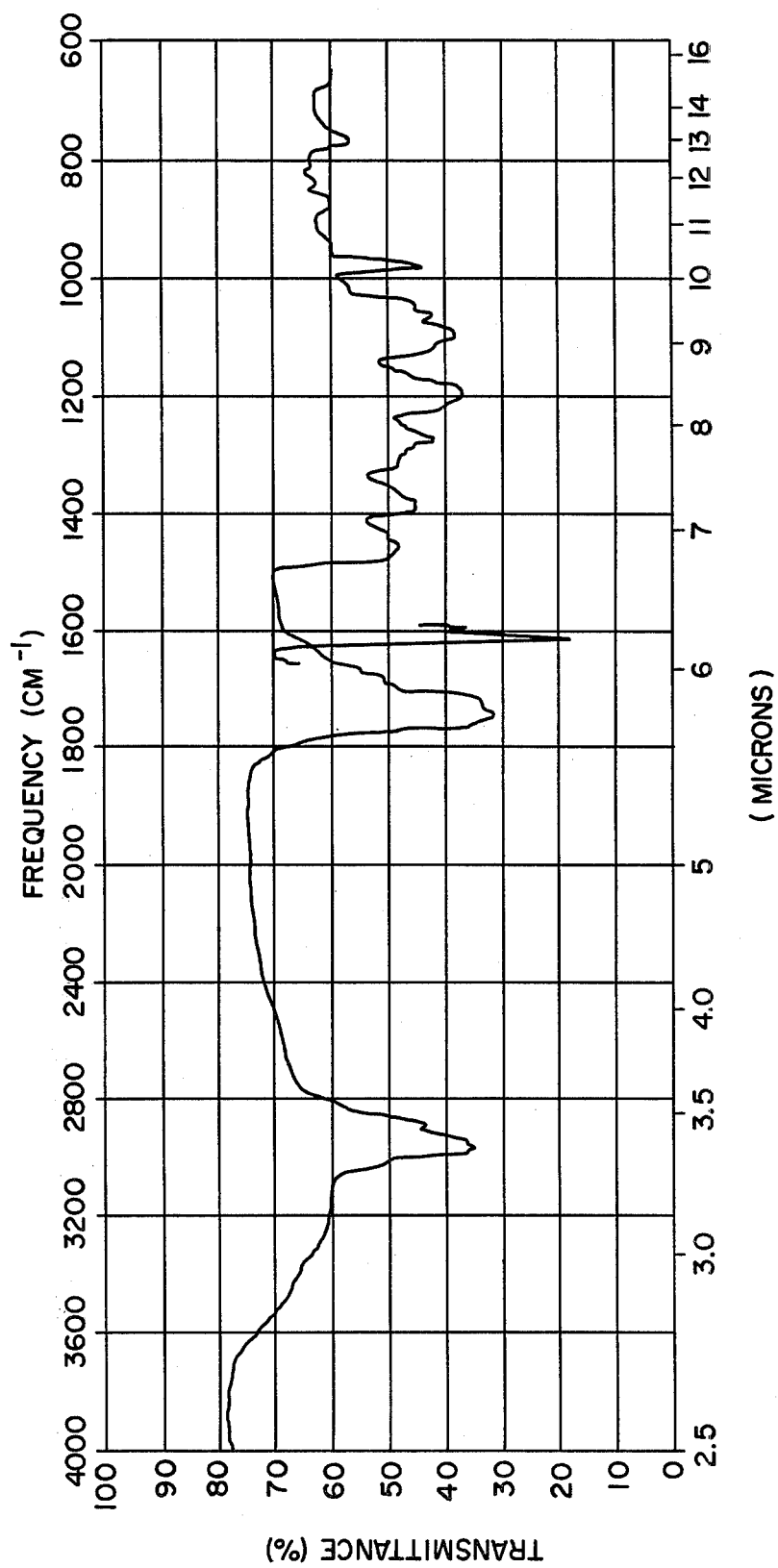
FIG. 3 depicts the infrared spectrum of acid S dibutyrate.

The novel diacyloxyacids of this invention derived from acid S have the formula I below:

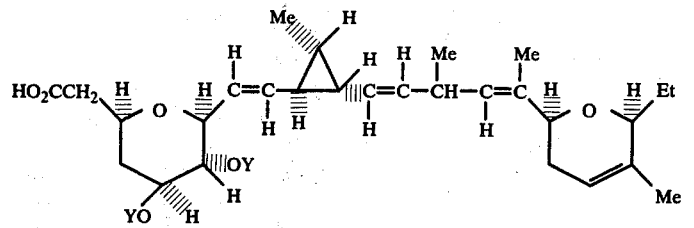

wherein Y in each instance, is an acyl group derived from formic acid or a lower alkyl carboxylic acid having from 3 to 7 carbon atoms. Preferably Y is an acyl group derived from formic acid or a lower alkyl carboxylic acid having from 3 to 4 carbon atoms. Acid S has the empirical formula $C_{28}H_{42}O_6$ and is represented by the above formula I wherein Y is hydrogen.

Acid S diacetate is disclosed and claimed in U.S. application Ser. No. 482,058, filed June 24, 1974, published as U.S. Application B482,058 on Mar. 2, 1976.

Acid S, as disclosed in U.S. Pat. No. 3,651,216, issued Mar. 21, 1972 and U.S. Pat. No. 3,804,948, issued Apr. 16, 1974 has the following characteristics:

Empirical Formula $C_{28}H_{42}O_6$ MW 474, infrared spectrum $v$ 870, 965, 1063, 1255, 1388, 1453, 1663, 1710, 2950, and 3400 cm.$^{-1}$, approximate $[\alpha]_D 25 +$ 36°, (chloroform, C = 0.7), Rf 0.56 [silica gel, ethyl acetate:isopropanol:water (85:15:5)].

Acid S is a potent antifungal substance, elaborated when the microorganism *Polyangium cellulosum* var. *fulvum* (ATCC No. 25532) is fermented in a suitable culture medium. The aforementioned patent (U.S. Pat. No. 3,804,948) also describes the chemical preparation of the methyl ester of acid S.

The organism designated *Polyangium cellulosum* var. *fulvum* is deposited at the American Type Culture Collection, and identified as ATCC 25532. All restriction on the availability of the culture deposit at ATCC will be irrevocably removed upon issuance of the instant application. The culture at ATCC will be maintained throughout the effective life of the patent.

According to the present invention, diacyloxy acids derived from acid S having the formula II:

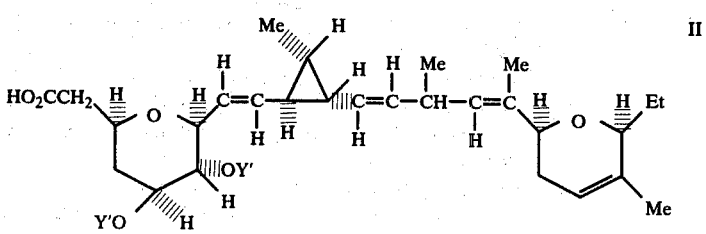

wherein Y' is an acyl group derived from a lower carboxylic acid having from 3 to 7 carbon atoms, preferably 3 to 4 carbon atoms, are prepared by reacting one equivalent of acid S having the formula III:

[Structure III: acid S showing HO₂CCH₂ group, cyclopropane ring with Me substituent, hydroxyl groups, conjugated diene system with Me substituents, and tetrahydropyran ring with Et and Me substituents]

with from about 100 to about 1,000 equivalents (preferably about 250 equivalents) of an appropriate acid anhydride in from about 200 to about 2,000 equivalents (preferably about 500 equivalents) of pyridine at room temperature overnight. Appropriate acid anhydrides are those derived from lower alkyl carboxylic acids having from 3 to 7 carbon atoms, preferably 3 or 4 carbon atoms. The reaction goes to completion within from about 12 to about 20 hours, typically by allowing the reaction to stand overnight at room temperature. Thus, one obtains the diacyloxyacids derived from acid S depicted in formula II above wherein Y' is an acyl group derived from a lower alkyl carboxylic acid having from 3 to 7 carbon atoms, preferably 3 to 4 carbon atoms.

In order to prepare acid S diformate, having formula IV:

[Structure IV: acid S diformate showing HO₂CCH₂ group, cyclopropane ring with Me substituent, formate ester groups (HCO—O— and —O—CH=O), conjugated diene system with Me substituents, and tetrahydropyran ring with Et and Me substituents]

one equivalent of acid S is reacted with about 4 equivalents of bromine and about 4 equivalents of triphenylphoshine in from about 100 to about 300 equivalents of dimethylformamide at about 0° C. Preferably, the reaction is conducted in an inert atmosphere, i.e., under nitrogen. The reaction is stored at about 0° C. for at least three days. Thus, acid S diformate, having the empirical formula $C_{30}H_{42}O_8$ and an infrared spectrum depicted in FIG. I is obtained.

The diacyloxyacids of this invention derived from acid S are characterized by infrared spectroscopy and mass spectrometry.

The infrared spectra of the diacyloxyacids of this invention derived from acid S are determined as thin films with an infrared absorption spectrometer equipped with a diffraction grating. In addition to providing spectral evidence for the chemical transformations of the processes of this invention, the infrared spectra of the compounds of this invention represent characteristic physical properties useful for their identification.

The mass spectra of the diacyloxyacids of this invention derived from acid S are measured on a double-focusing high resolution mass spectrometer utilizing a heated direct insertion probe. The molecular composition of the parent peaks are determined by employing perfluorotributylamine (mass spectral grade, available from PCR, Inc., Gainsville, Florida) as the internal standard and peak matching techniques well-known to those skilled in the art. The application of these mass spectral techniques permits not only the determination of the molecular composition of the parent ion and confirmation of the postulated transformations, but, like the aforementioned infrared measurements, provides a definitive physical property useful for identification purposes.

The novel diacyloxyacids of this invention derived from acid S inhibit the growth of a variety of fungi, including *Histoplasma capsulatum* and *Microsporum fulvum*. Minimum inhibitory concentrations falling within the range of from 50 to 1.56 micrograms/milliliter are obtained when evaluated by the in vitro tube dilution technique described in U.S. Pat. No. 3,651,216. Thus, the compounds of the present invention are useful in the treatment of dermatophytic and systemic fungal diseases.

The novel diacyloxyacids of this invention derived from acid S are also active against gram positive bacteria, showing minimum inhibitory concentrations in the range of 25 to 6.25 micrograms/milliliter against *Streptococcus pyogenes*. Thus, the compounds of the invention are useful antibacterial agents.

The novel antibacterial, antifungal substances of this invention can be formulated with inert excipients into various dosage forms for oral, parenteral and topical administration by methods well-known to those skilled in the pharmacist's art. Tablets, capsules, powders, solutions, suspensions, ointments, gels and creams are included among these dosage forms.

The diacyloxyacids of this invention derived from acid S can be administered orally, parenterally or topically to various mammals, such as dogs, cats and guinea pigs, afflicted with fungal or bacterial diseases. The effective dosage range is about 0.01 to about 100 mg/kg of body weight for the treatment of a fungal disease. For the treatment of bacterial infections, from about 0.01 to about 100 mg/kg of body weight is recommended.

The following examples are included to further illustrate the invention but are not to be construed as limiting the scope of the invention.

EXAMPLE 1

Acid S Diformate

A solution of acid S (118 mg 1 equivalent) in dimethylformamide (1 ml) is added to a solution of triphenylphosphine (262 mg, 4 equivalents) and bromine (160 mg, 4 equivalents) in dimethylformamide (2.5 ml) at 0° C. under nitrogen with stirring. The resulting solution is stored at 0° C. for 3 days. The reaction mixture is poured into saturated brine (10 ml) and extracted with ether (3 × 10 ml). The extracts are dried over $MgSO_4$ and evaporated to give a brown gum. The product is isolated by preparative thin layer chromatography as a colorless gum (35 mg, 26%). Diagnostic thin-layer chromatography indicates a pure homogeneous product.

Empirical formula: $C_{30}H_{42}O_8$.
Molecular weight: 530.

Infrared Spectrum: $\nu$ max 2700–2350cm$^{-1}$ (OH of $CO_2H$), 1740 (C = O of formates), 1720 (CO of $-CO_2H$)

Mass Spectrum: observed molecular ion 530.2930; calculated $C_{30}H_{42}O_8$ 530.2878.

EXAMPLE 2

Acid S Dipropionate

A solution of acid S (20 mg) in propionic anhydride (1 ml) and pyridine (2 ml) is allowed to stand at room temperature overnight. Water (2 ml) is added and the solvents are removed at reduced pressure to give the crude product. The product is purified by preparative thin-layer chromatography to give a colorless gum (15 mg, 60%). Diagnostic thin-layer chromatography indicated a pure homogeneous product.

Empirical formula: $C_{34}H_{50}O_8$.
Molecular weight: 586.

Infrared Spectrum: $\nu$ max 2800–2300 cm$^{-1}$ (OH of $-CO_2H$), 1745 (C = O of propionates), 1720 (CO of $-CO_2H$)

Mass Spectrum: observed molecular ion 586.3193; calculated for $C_{34}H_{50}O_8$ 586.3505.

m/e (relative intensity) 586 (9), 568 (2), 557 (33), 491 (11) and 193 (100).

EXAMPLE 3

Acid S Dibutyrate

A solution of acid S (20 mg) in butyric anhydride (1 ml) and pyridine (2 ml) is allowed to stand at room temperature overnight. Water (2 ml) is added and the solvents are removed at reduced pressure to give the crude product. The product is purified by preparative thin-layer chromatography to give a colorless oil (15 mg, 57%). Diagnostic thin-layer chromatography indicated a pure homogeneous product.

Empirical formula: $C_{36}H_{54}O_8$.
Molecular weight: 614.

Infrared Spectrum: $\nu$ max 2800–2400cm$^{-1}$ (OH of $-CO_2H$), 1745 (C = O of butyrates), 1720 (C = O of $-CO_2H$)

Mass Spectrum: observed molecular ion 614.3643; calculated for $C_{36}H_{54}O_8$ 614.3818.

m/e (relative intensity) 614 (10), 585 (20), 519 (10), 245 (30), 215 (90) and 193 (100).

We claim:

1. A compound having the formula I:

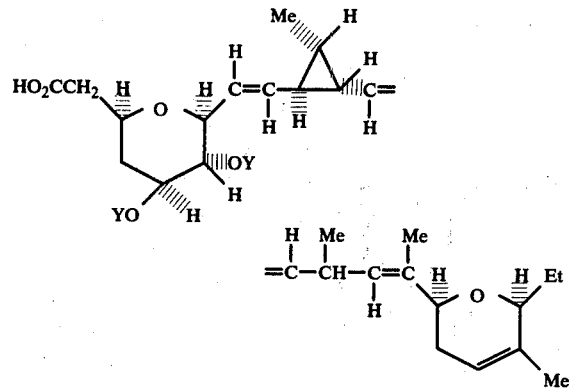

wherein Y is an acyl group derived from formic acid or derived from a lower alkyl carboxylic acid having from 3 to 7 carbon atoms.

2. A compound according to claim 1 which is acid S diformate having the formula:

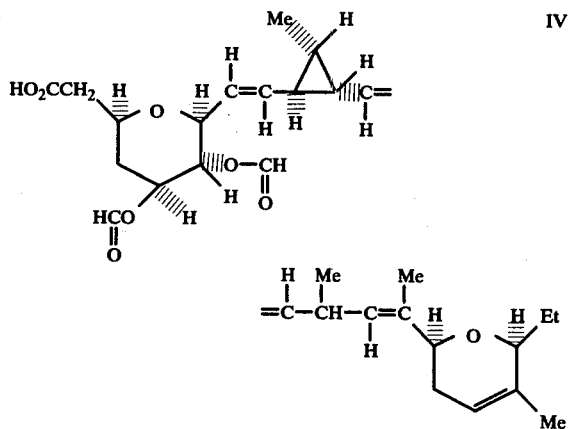

3. A compound according to claim 1 which is acid S dipropionate having the formula:

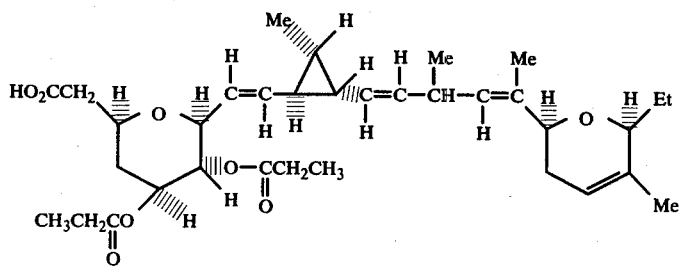

4. A compound according to claim 1 which is acid S dibutyrate having the formula:

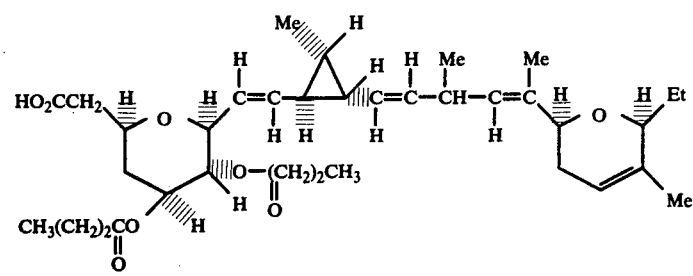
5. A process for preparing the antibiotic substance, acid S diformate having formula IV:
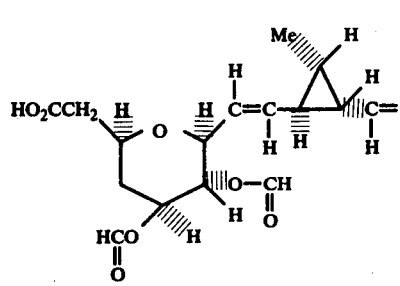
IV
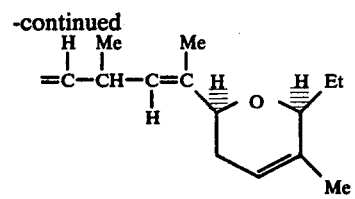
which comprises reacting one equivalent of acid S having the formula III:
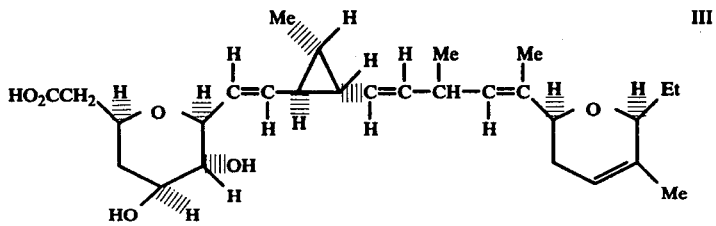
III
with about 4 equivalents of bromine and about 4 equivalents of triphenylphosphine in from about 100 to about 300 equivalents of dimethylformamide at about 0° C. for at least three days.
* * * * *